United States Patent
Staraj et al.

(10) Patent No.: US 12,250,924 B2
(45) Date of Patent: Mar. 18, 2025

(54) METHOD, FACILITY AND TAG FOR TRACKING THE ACTIVITY OF ANIMALS IN CAPTIVITY

(71) Applicants: CENTRE NATIONAL DE LA RECHERCHE SCIENTIFIQUE, Paris (FR); UNIVERSITÉ CÔTE D' AZUR, Nice (FR)

(72) Inventors: Robert Staraj, Saint-Paul de Vence (FR); Georges Carle, Nice (FR); Philippe Perrisol, Opio (FR); Philippe Le Thuc, Grasse (FR); Aliou Diallo, Nice (FR)

(73) Assignees: CENTRE NATIONAL DE LA RECHERCHE SCIENTIFIQUE, Paris (FR); UNIVERSITE CÔTE D'AZUR, Nice (FR)

( * ) Notice: Subject to any disclaimer, the term of this patent is extended or adjusted under 35 U.S.C. 154(b) by 386 days.

(21) Appl. No.: 17/593,431

(22) PCT Filed: Mar. 16, 2020

(86) PCT No.: PCT/EP2020/057103
§ 371 (c)(1),
(2) Date: Sep. 17, 2021

(87) PCT Pub. No.: WO2020/193252
PCT Pub. Date: Oct. 1, 2020

(65) Prior Publication Data
US 2022/0151197 A1    May 19, 2022

(30) Foreign Application Priority Data
Mar. 22, 2019 (FR) .................................. 1903004

(51) Int. Cl.
*A01K 1/03* (2006.01)
*A01K 29/00* (2006.01)
(Continued)

(52) U.S. Cl.
CPC ............ *A01K 1/031* (2013.01); *A01K 29/005* (2013.01); *G06K 7/10356* (2013.01); *H01Q 7/00* (2013.01)

(58) Field of Classification Search
CPC .. A01K 1/031; A01K 29/005; G06K 7/10356; H01Q 7/00
(Continued)

(56) References Cited

U.S. PATENT DOCUMENTS 4,274,083 A * 6/1981 Tomoeda ................ G01S 13/82
119/51.02
5,482,008 A    1/1996 Stafford et al.
(Continued)

FOREIGN PATENT DOCUMENTS

CN    103971157 A    8/2014

OTHER PUBLICATIONS

Tesla Modely 3 Key Ring Teslarati (https://www.teslarati.com/tesla-model-3-key-card-ring-diy-project/tesla-modely-3-key-ring-2/) (Year: 2021).*
(Continued)

*Primary Examiner* — Tye William Abell
*Assistant Examiner* — Maria E Graber
(74) *Attorney, Agent, or Firm* — Greer, Burns & Crain, Ltd

(57) ABSTRACT

A method for tracking the activity of animals confined in a facility including at least one cage, a plurality of antennae arranged underneath the at least one cage, an RFID reader to which the plurality of antennae are connected, a computer capable of controlling transmission and reception by the
(Continued)

RFID reader, and an RFID tag to be fitted to an animal confined in the cage, the method including that the following steps are carried out:—the animal is fitted with the tag,—the RFID reader generates the transmission of an electromagnetic wave at the plurality of antennae,—the RFID reader identifies which antenna(e) has/have received the response transmitted by the tag,—the computer analyses over a given period which antennae have received a signal transmitted by the tag, thus determining the consecutive positions of the animal.

19 Claims, 2 Drawing Sheets

(51) Int. Cl.
    *G06K 7/10*         (2006.01)
    *H01Q 7/00*         (2006.01)

(58) Field of Classification Search
    USPC .......................................................... 119/421
    See application file for complete search history.

(56) References Cited

U.S. PATENT DOCUMENTS

| | | | | |
|---|---|---|---|---|
| 6,400,338 | B1* | 6/2002 | Mejia | H01Q 1/2225 |
| | | | | 343/788 |
| 7,554,501 | B2* | 6/2009 | Park | H01Q 1/38 |
| | | | | 343/866 |
| 9,648,848 | B2* | 5/2017 | Weelink | A01K 5/001 |
| 9,680,225 | B2* | 6/2017 | Seo | G02F 1/00 |
| 10,229,299 | B2* | 3/2019 | Staraj | G06K 7/10366 |
| 10,595,513 | B2* | 3/2020 | Halachmi | A01K 29/005 |
| 10,639,014 | B2* | 5/2020 | Biondi | A61D 17/00 |
| 10,825,549 | B2* | 11/2020 | Betts-Lacroix | A01K 1/031 |
| 11,432,531 | B2* | 9/2022 | Villalobos | A01K 5/01 |
| 2005/0248460 | A1 | 11/2005 | Mejia et al. | |
| 2009/0009335 | A1* | 1/2009 | Stewart | G06K 7/10336 |
| | | | | 340/572.7 |
| 2017/0111128 | A1* | 4/2017 | Hammerschmidt | |
| | | | | A01K 11/006 |
| 2018/0146645 | A1* | 5/2018 | Arbel | A01K 11/006 |
| 2018/0253517 | A1 | 9/2018 | Kimchi et al. | |
| 2020/0288677 | A1* | 9/2020 | Claessens | A01K 11/006 |
| 2020/0323170 | A1* | 10/2020 | Garigan | A01K 27/009 |
| 2021/0007327 | A1* | 1/2021 | Weyer | A01K 11/006 |

OTHER PUBLICATIONS

DIY Tesla Key Tesla Motors Club (https://teslamotorsclub.com/tmc/threads/diy-tesla-key.234388/) (Year: 2021).*
Bio Implant Chip Tesla Model 3 Hack Project posted by Amie DD on hackaday.io (available at https://hackaday.io/project/162200/logs) (Year: 2019).*
International Search Report and Written Opinion received for PCT/EP2020/057103, mailed May 20, 2020.
French Search Report received for Application No. 1903004, dated Dec. 3, 2019.

* cited by examiner

[Fig. 1]
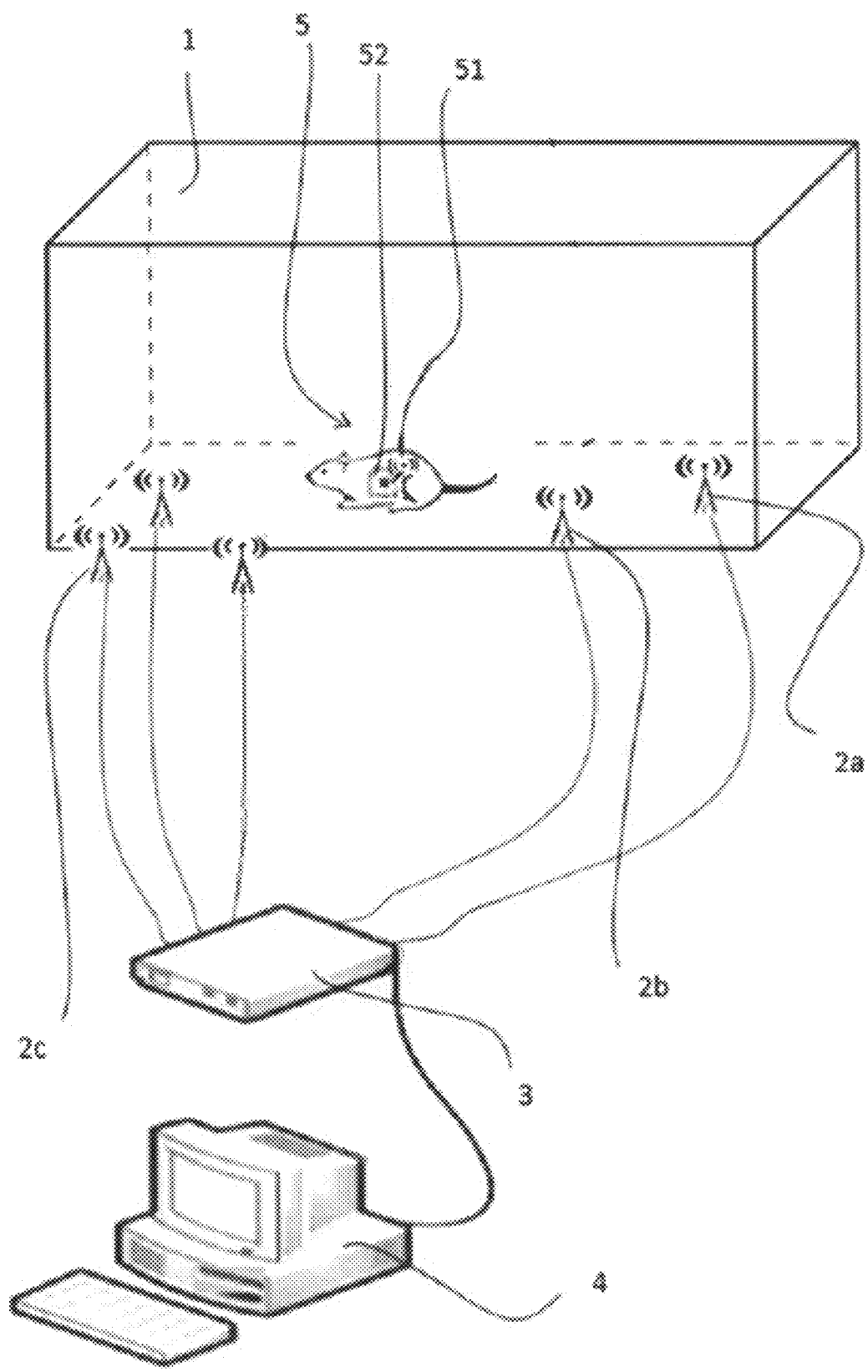

[Fig. 2]
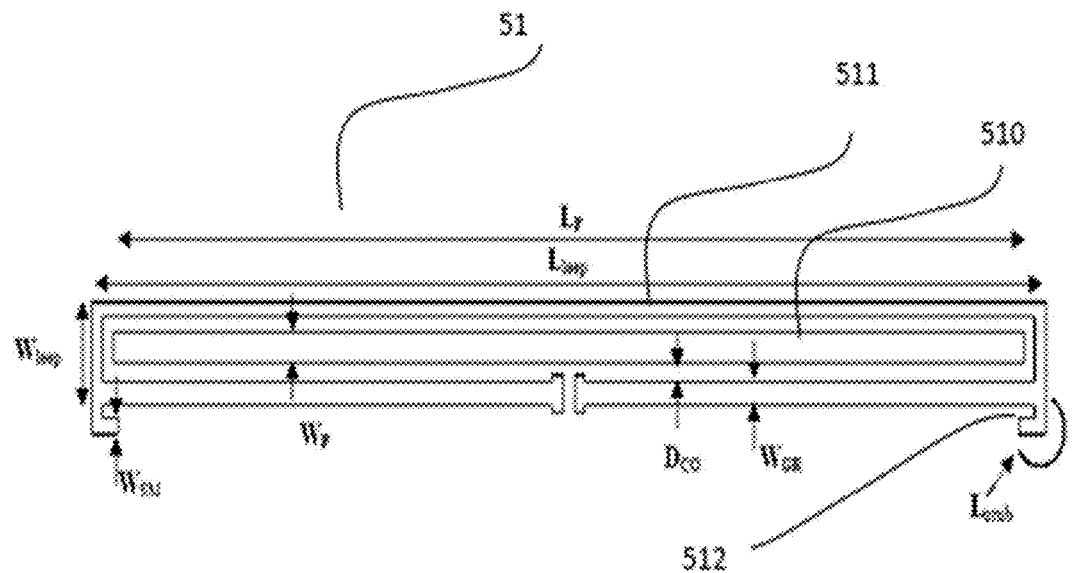
[Fig. 3]
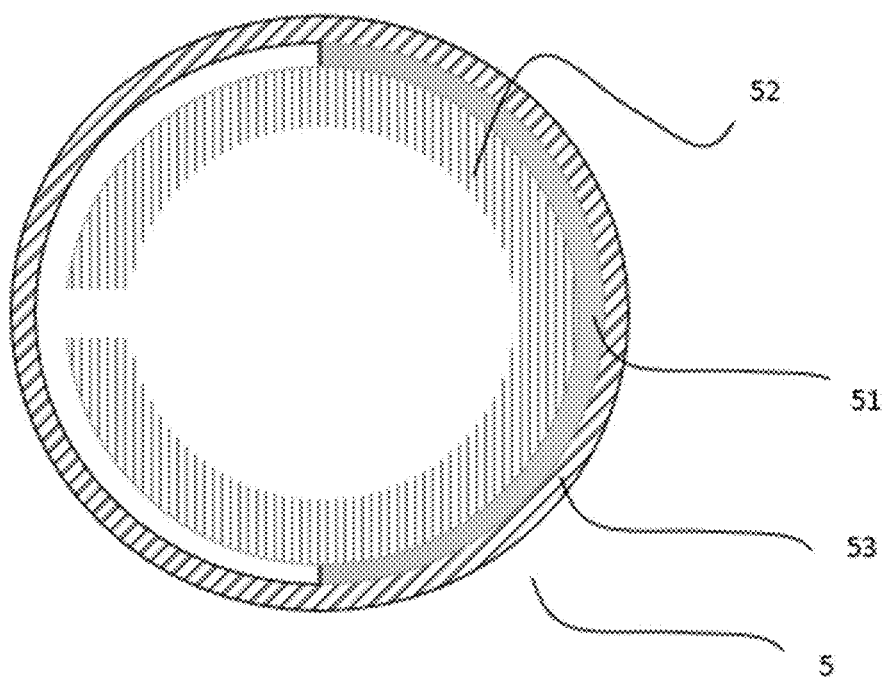

METHOD, FACILITY AND TAG FOR TRACKING THE ACTIVITY OF ANIMALS IN CAPTIVITY

BACKGROUND

A subject of the present invention is a method and a facility for tracking the activity of animals housed in confined conditions, as well as a tag intended to be fitted to an animal housed in confined conditions.

Tracking the activity of animals housed in confined conditions in various contexts, whether pre-operatively, post-operatively, in a clinical or laboratory setting, requires daily observation by a competent person.

The use of automated surveillance systems without human intervention is therefore preferable, for taking and analysing the vital signs of the animals, inasmuch as these systems do not disturb the animal, do not cause it any harm, and do not raise its anxiety level.

Surveillance techniques also make it possible to obtain more accurate results, inasmuch as they avoid the "white coat syndrome". Thus, it has been shown that the reading of vital data supplied by invasive implants, such as temperature, glucose level and other physiological data, by a human participant in proximity to the animal, was in fact disturbed.

More particularly, it has been established that systematically, animals react negatively or positively to the proximity of humans, and that the act itself of attempting to obtain readings of the data supplied by invasive implants affects the data.

In parallel with this observation, animal welfare, as well as the pain and distress that animals used for scientific purposes may feel, have long been a concern of the general public and of the research community.

In fact there exists a Directive 2010/63/EU of the European Parliament and of the Council of 22 Sep. 2010 on the protection of animals used for scientific purposes, transposed into French law in Decree 2013-118 of 1 Feb. 2013, on the protection of animals used for scientific purposes.

It was these concerns, combined with the increasing use of animals in fundamental and applied research, that motivated W. M. S. Russell and R. L. Burch to examine how decisions should be taken with respect to such use of animals.

In the work "The Principles of Humane Experimental Technique" (principles of ethical experimental technique), the first edition of which dates from 1959, the authors Russell and Burch propose to implement the "Three Rs" principle, which advocates replacement, reduction, and refinement. For some forty years, this Three Rs principle has been widely recognized as an established ethical principle in the context of science making use of animals.

A certain number of studies relating to the development of facilities for tracking the activities of animals housed in confined conditions have been undertaken.

Thus, documents US 2017/111128 A1 and US 2018/253517 A1 refer to methods and facilities for tracking the activity of animals housed in confined conditions in a facility formed of a cage, a plurality of antennas arranged under the cage, an RFID reader to which the plurality of antennas is linked, computerized means capable of controlling the RFID reader to transmit and receive, and an RFID tag intended to be fitted to an animal housed in confined conditions in the cage.

SUMMARY

However, with the aim of improving the accuracy of the collected data, it has proved necessary to improve the RFID tags intended to be fitted to the animals.

To this end, the invention proposes a facility for tracking the activity of animals housed in confined conditions, the facility including at least one cage, a plurality of antennas arranged under the at least one cage, a reader to which the plurality of antennas is linked, computerized means capable of controlling the reader to transmit and receive, and a tag intended to be fitted to an animal housed in confined conditions in the cage, the tag comprising an antenna and a chip both encapsulated in a capsule made from biocompatible material, the antenna having, in the developed mode, a central plate extending longitudinally and surrounded by an open loop having two elbowed stubs.

Optional characteristics of the invention, which can be additional or substitutions, are disclosed hereinafter.

According to certain optional characteristics, the surface area of the cage is less than 1 metre, the cage measuring between 10 and 30 cm wide and 25 to 75 cm long.

According to other optional characteristics, at least four antennas are distributed under the cage, preferably between six and eight antennas.

Preferably, the reader is an RFID reader.

Preferably, the tag is a passive RFID tag equipped with an antenna affixed on a chip associated with an identifier.

Preferably, the antenna and the chip are encapsulated in a capsule made from biocompatible material so that the tag can be injected by the subcutaneous route.

A further purpose of the invention is a tag intended to be fitted to an animal housed in confined conditions in a facility according to an embodiment of the invention, the tag comprising an antenna and a chip both encapsulated in a capsule made from biocompatible material, the antenna having, in the developed mode, a central plate extending longitudinally and surrounded by an open loop having two elbowed stubs.

Optional characteristics of the invention, which can be additional or substitutions, are disclosed hereinafter.

According to certain optional characteristics, the length of the loop LLOOP is less than 20 mm, preferably substantially of the order of 17.4 mm, the width of the loop WLOOP is less than 2 mm, preferably substantially of the order of 1.4 mm, the length of the central plate LP is less than 20 mm, preferably substantially of the order of 16.6 mm, the width of the central plate WP is less than 1 mm, preferably substantially of the order of 0.45 mm, the length of the elbowed stubs Lstub is less than 1 mm, preferably substantially of the order of 0.9 mm.

Preferably, the antenna is constituted by a conductive material, preferably copper, while the chip is constituted by a composite material, preferably a PTFE-reinforced glass.

A further purpose of the invention is a method for tracking the activity of animals housed in confined conditions, in a facility including at least one cage, a plurality of antennas arranged under the at least one cage, an RFID reader to which the plurality of antennas is linked, computerized means capable of controlling the RFID reader to transmit and receive, and an RFID tag intended to be fitted to an animal housed in confined conditions in the cage, the tag comprising an antenna and a chip both encapsulated in a capsule made from biocompatible material, the antenna having, in the developed mode, a central plate extending longitudinally and surrounded by an open loop having two elbowed stubs, characterized in that the following steps are carried out:

the animal is fitted with the tag,
the RFID reader generates the transmission of an electromagnetic wave at the plurality of antennas, the RFID reader identifies the one (or more than one) of the plurality of antennas that has(have) received the response transmitted by the RFID tag, such that the position of the animal is determined as a function of the antenna or antennas that has or have received the response transmitted by the RFID tag.

Optional characteristics of the invention, which can be additional or substitutions, are disclosed hereinafter.

According to certain optional characteristics, the computerized means analyse, over a given time period, which antennas have received a signal transmitted by the RFID tag and thus determine the successive positions of the animal.

According to other optional characteristics, the computerized means determine the position of the animal by means of algorithms based on triangulation methods or by means of positioning algorithms based on fingerprinting.

According to other optional characteristics, the surface area of the cage is less than 1 metre, the cage measuring between 10 and 30 cm wide and 25 to 75 cm long.

According to other optional characteristics, at least four antennas are distributed under the cage, preferably between six and eight antennas.

According to other optional characteristics, the animal is fitted with the tag by subcutaneous injection of said tag, said tag including an antenna and a chip encapsulated in a capsule made from biocompatible material.

According to other optional characteristics, the length of the loop LLOOP is less than 20 mm, preferably substantially of the order of 17.4 mm, the width of the loop WLOOP is less than 2 mm, preferably substantially of the order of 1.4 mm, the length of the central plate LP is less than 20 mm, preferably substantially of the order of 16.6 mm, the width of the central plate WP is less than 1 mm, preferably substantially of the order of 0.45 mm, the length of the elbowed stubs Lstub is less than 1 mm, preferably substantially of the order of 0.9 mm.

According to other optional characteristics, the antenna is constituted by a conductive material, preferably copper, while the chip is constituted by a composite material, preferably a PTFE-reinforced glass.

According to other optional characteristics, the RFID tag transmits signals conveying items of information on the physiological state of the animal.

BRIEF DESCRIPTION OF THE DRAWINGS

Other advantages and characteristics of the invention will become apparent on reading the detailed description of implementations and embodiments that are in no way limitative, and from the following attached drawings:

FIG. 1 This figure is a diagrammatic view of a facility for tracking the activity of animals housed in confined conditions, according to an embodiment of the invention.

FIG. 2 This figure is a top view of an element constituting a tag intended to be fitted to an animal housed in confined conditions, the tag being according to an embodiment of the invention.

FIG. 3 This figure is a cross section view of a tag intended to be fitted to an animal housed in confined conditions, the tag being according to an embodiment of the invention.

DETAILED DESCRIPTION

For reasons of clarity and brevity, the references on the figures correspond to the same elements.

As the embodiments described hereinafter are in no way limitative, variants of the invention can be considered comprising only a selection of the characteristics described, in isolation from the other characteristics described, (even if this selection is isolated within a phrase comprising these other characteristics), if this selection of characteristics is sufficient to confer a technical advantage or to differentiate the invention with respect to the state of the prior art.

This selection comprises at least one, preferably functional, characteristic without structural details, or with only a part of the structural details if this part alone is sufficient to confer a technical advantage or to differentiate the invention with respect to the state of the prior art.

FIG. 1 describes a facility for tracking the activity of animals housed in confined conditions, according to an embodiment of the invention.

The facility includes a cage 1 having a surface area less than 1 square metre, i.e. a cage intended for small animals such as for example rodents.

Preferably, the cage measures between 10 and 30 cm as regards the width, and between 25 and 75 cm as regards the length.

A plurality of antennas 2a, 2b, 2c is arranged under the cage, preferably between four and eight antennas.

The plurality of antennas 2a, 2b, 2c is linked to a reader 3 controlled to transmit and receive by computerized means 4.

Of course, the facility can include a plurality of cages, each of the cages being equipped with a set of antennas arranged under the cage.

The sets of antennas can be connected as a whole to one and the same reader controlled to transmit and receive by centralized computerized means.

The facility also includes a tag 5 intended to be fitted to an animal housed in confined conditions in the cage.

This tag is capable of receiving the signals transmitted by the antennas arranged under the cage when it is situated within their respective field.

This tag is also capable of receiving the intensity of the signals (called RSSI level of the signal) transmitted by the antennas arranged under the cage.

This tag is also capable of transmitting a signal in response, which is in turn received by the transmitting antenna and transmitted to the reader.

The reader thus transmits to the computerized means a succession of items of information that indicate which antennas have been polled by the proximity of the tag.

It then becomes possible to determine approximately the successive locations of the animal bearing the tag.

Preferably, the reader 3 is an RFID reader associated with the tag 5, which also uses RFID technology.

Preferably, the tag 5 is a passive RFID tag equipped with an antenna 51 affixed on a chip 52 associated with an identifier.

Preferably, the antenna 51 and the chip 52 are encapsulated in a capsule made from biocompatible material, in such a way that the tag can be injected by the subcutaneous route.

In fact, in order to implant a tag in a small laboratory animal, it is preferable to use adapted injectors (or syringes), as they make it possible to avoid carrying out surgical procedures and can be used by zootechnicians who are not authorized for surgery.

It will be noted that the capsule can contain, in addition to a small antenna, other components such as sensors, electronic chips or even additionally a camera or battery.

The tag 5 can be based on the format of the TAM-M® chip from the company Intellibio. This tag has the form of a capsule of dimension 1.4×8 mm, made from biocompatible glass and coated with Parylene in order to avoid migration.

It offers a much longer lifetime than that of the small laboratory animals and has good read performance. Its memory is write-programmable with 96 alphanumeric characters.

Thus, the tag can incorporate a large number of items of information on the physiological state of the animal.

The tag 5, which constitutes one of the subjects of the invention, will now be described in greater detail.

Firstly, it is recalled that tracking the small animals used in the context of laboratory tests and remote analysis of their behaviour, at low cost and in real time, has been the subject of numerous research studies.

A major problem lies in the difficulty of implanting miniature wireless sensors which require highly technical components, the most difficult being the antenna.

In fact, the main difficulty in the design of antennas for bio-implantable communication devices is to supply an efficient radiant structure, this despite the volume constraints and the high impact of the surrounding biological tissues.

Although numerous studies have involved the use of implanted antennas in the Medical Implant Communications Service (MICS) band (402-405 MHz), it should be noted that at these frequencies, the size of the antennas can be a real drawback in the case of small animals, hence a search for miniaturization.

An alternative consists of the use of Radio-Frequency Identification (RFID) technology in the UHF band from 860 to 960 MHz.

In fact, it has two predominant advantages: it facilitates the implantation of the tag and does not require the addition of a battery to supply the implanted peripheral.

After producing a link budget analysis making it possible to calculate the minimum performance of the implanted antenna to be designed for reliable and efficient communication, a 3D passive RFID tag was optimized by different techniques to achieve final structures that could be implanted or injected in the back of a mouse.

This 3D passive RFID tag has the following specifications:

European RFID frequency band: 865-868 MHz
Maximum permitted dimensions: 20×2×1 mm$^3$
Minimum range: 5.8 cm
Impedance of the chip used: Impinj Monza R6 13−j126 Ohm
Impedance of the proposed antenna: 13+j126 Ohm As shown in FIG. 3, the tag comprises an antenna 51 and a chip 52 both encapsulated in a capsule 53.

The chip 52 is a substrate made from composite material, in this case a PTFE-reinforced glass, e.g. for example RT5880 Duroid, which has a relative permittivity of the order of 2.2, a dissipation factor of the order of 0.0009 and a thickness of the order of 0.127 mm.

As the capsule must be biocompatible, it can be made using a prestressed borosilicate glass tube, which advantageously has a high resistance to impact and scratching.

This material has a relative permittivity of the order of 4.6, a dissipation factor of the order of 0.0037, a thickness of the order of 0.1 mm and a diameter of the order of 1.6 mm.

The layer of borosilicate glass has the function of preventing the possibility of rejection of the implant by the animal's body, and also to facilitate the transition of the radiant wave between the implanted antenna and the animal tissues.

As shown in FIG. 2, the antenna 51 is produced from a copper plate.

In the developed mode, the antenna 51 has a central plate 510 surrounded by an open loop 511 provided with two elbowed stubs 512.

The length of the loop 511 LLOOP is less than 20 mm, preferably substantially of the order of 17.4 mm.

The width of the loop WLOOP is less than 2 mm, preferably substantially of the order of 1.4 mm.

The length of the central plate 510 LP is less than 20 mm, preferably substantially of the order of 16.6 mm.

The width of the central plate WP is less than 1 mm, preferably substantially of the order of 0.45 mm.

The length of the elbowed stubs Lstub is less than 1 mm, preferably substantially of the order of 0.9 mm.

This geometry, which corresponds to a very low total volume for the antenna (since of the order of 36.2 mm$^3$) makes it possible to obtain an impedance of 13.4+j126,3 Ohms with a total gain of −23.4 dBi and an efficiency of 0.2%.

These values are very acceptable with respect to the conventional antennas that are bulkier and operate at these frequencies.

The method for tracking the activity of animals housed in confined conditions in a facility such as described above, will now be described, it being understood that there is at least one small animal confined in a cage 1 with a surface area less than 1 square metre, a plurality of antennas 2a, 2b, 2c being arranged under the cage, and linked to a RFID reader 3, computerized means 4 being capable of controlling the RFID reader to transmit and receive.

According to a prior step, it is necessary to fit the animal with the tag 5.

Then, the RFID reader 3 generates the emission of an electromagnetic wave at the plurality of antennas 2a, 2b, 2c.

Then, the RFID reader 3 identifies which one or ones of the plurality of antennas has or have received the response transmitted by the RFID tag, such that the position of the animal is determined as a function of the antenna or antennas that has or have received the response transmitted by the RFID tag.

The computerized means 4 are then able to analyse over a given time period which antennas have received a signal transmitted by the RFID tag and thus determine the successive positions of the animal.

The computerized means 4 can then determine the position of the animal by means of algorithms based on triangulation methods or by means of positioning algorithms based on fingerprinting, or by means of WLAN indoor positioning algorithms.

These algorithms use the received signal strength indicator (RSSI), which is a value that quantifies the power level of the electromagnetic waves (intensity of the measured signal) received by the receiver antenna. The closer the source, the stronger the radio signal and the higher the RSSI level.

The RSSI is estimated differently according to the telecommunication technologies used. For example, for the 4G mobile network, the RSSI is measured only on the allocated carriers, while for Wi-Fi or the 3G network, it is necessary to measure it only on the frequency band.

As regards the RFID technology, the RSSI value is measured over its entire allocated frequency band.

The values can then be obtained with a software program on a local computer.

It can be concluded that the system is operating correctly when the value received from the tag is greater than the sensitivity of the reader.

Turning now to the algorithms, those of the fingerprinting type and those of the WLAN indoor positioning algorithm type are particularly suitable in the case of indoor geolocation difficulties in confined spaces.

The fingerprinting signal approach comprises two steps: calibration and location.

The calibration phase comprises the acquisition of characteristics (generally intensity, called RSSI) of the signals originating from the stationary transmitters (beacons) at predefined points, which are used to construct a database that corresponds to the collected values (digital fingerprints) with the corresponding sites.

During the location phase, the mobile device acquires a fingerprint of the signal and the positioning system uses the calibration data, coupled to the appropriate algorithms, to determine the best correspondence for the site to which the fingerprint most probably belongs.

The approach with the WLAN (wireless local area network) positioning algorithm uses a very widespread communication system (better known as "Wi-Fi network").

This algorithm is constituted by two phases, "off-line measurement" and "on-line measurement", which also incorporate different positioning algorithms of the NN (nearest neighbours) or KNN (K-nearest neighbours) type.

Thus, the facility and the method according to the invention allow accurate recording of the movements of a laboratory animal housed in confined conditions.

The data collected by the facility can also be made available to artificial intelligence technologies.

It thus becomes possible to analyse the behaviour and the movements of the small laboratory animals by using deep learning.

This is an artificial intelligence technology aiming to anticipate particular behaviours on the basis of a certain number of items of information.

These data make it possible to demonstrate for example the stereotypies of these animals, stereotypies being conventionally defined as repetitive, invariable behaviours which have no apparent aim or function.

Based on these data, it is for example possible to determine if the activity of the animal is a reactive or pathological, behavioural or organic manifestation.

It should be noted that the different characteristics, forms, variants and embodiments of the invention can be combined together in various combinations, provided they are not incompatible or mutually exclusive.

The invention claimed is:

1. A facility for tracking the activity of animals housed in confined conditions the facility comprising:
   at least one cage;
   a plurality of antennas of the at least one cage arranged under the at least one cage;
   a reader to which the plurality of antennas is linked;
   a computer processor configured for controlling the reader to transmit and receive;
   a tag configured for being fitted to an animal housed in confined conditions in the at least one cage;
   the tag comprising an antenna of the tag, being separate from said plurality of antennas, and being made from a conductive material and a chip made from a composite material, both encapsulated in a capsule made from biocompatible material so that the chip is separated from said capsule by said antenna; and
   the antenna of the tag comprising a central plate independent from the chip, the central plate extending longitudinally and surrounded by an inner side of an open loop with interrupted ends and comprising two elbowed stubs, said stubs extending laterally and externally from the open loop.

2. The facility for tracking the activity of animals housed in confined conditions according to claim 1, characterized in that the surface area of the cage is less than 1 metre, the cage measuring between 10 and 30 cm wide and 25 to 75 cm long.

3. The facility for tracking the activity of animals housed in confined conditions according to claim 1, characterized in that the plurality of antennas arranged under the at least one cage comprises at least four antennas distributed under the cage.

4. The facility for tracking the activity of animals housed in confined conditions according to claim 1, wherein the open loop defines an opening when viewed from above, the open loop further defining a plurality of corners, the elbowed stubs each projecting laterally from an associated one of the corners.

5. The facility for tracking the activity of animals housed in confined conditions according to claim 1, wherein the reader is an RFID reader associated with the tag—and wherein the tag is an RFID tag.

6. The facility for tracking the activity of animals housed in confined conditions according to claim 5, wherein the tag is a passive RFID tag equipped with the antenna of the tag affixed on the chip associated with an identifier.

7. The facility for tracking the activity of animals housed in confined conditions according to claim 6, characterized in that the antenna of the tag and the chip are encapsulated in the capsule made from biocompatible material in such a way that the tag can be injected by the subcutaneous route.

8. A tag configured for being fitted to an animal housed in confined conditions in a facility for tracking the activity of animals housed in confined conditions, the facility comprising:
   at least one cage;
   a plurality of antennas of the cage arranged under the at least one cage;
   a reader to which the plurality of antennas of the cage is linked;
   a computer processor configured for controlling the reader to transmit and receive;
   a tag configured for being fitted to an animal housed in confined conditions in the at least one cage;
   the tag comprises an antenna of the tag, separate from said plurality of antennas, and a chip both encapsulated in a capsule made from biocompatible material; and
   the antenna of the tag comprising a central plate independent from the chip extending longitudinally and said central plate being surrounded by an inner side of an open loop with two interrupted ends and comprising two elbowed stubs, said stubs extending laterally and externally from the open loop.

9. The tag configured for being fitted to an animal housed in confined conditions according to claim 8, characterized in that the length of the open loop LLOOP is less than 20 mm, the width of the open loop WLOOP is less than 2 mm, the length of the central plate LP is less than 20 mm, the width of the central plate WP is less than 1 mm, the length of each elbowed stub Lstub is less than 1 mm.

10. The tag configured for being fitted to an animal housed in confined conditions according to claim 8, characterized in that the antenna of the tag is constituted by a conductive material.

11. The tag configured for being fitted to an animal housed in confined conditions according to claim 8, wherein the open loop defines an opening when viewed from above, the open loop further defining a plurality of corners, the elbowed stubs each projecting laterally from an associated one of the corners.

12. A method for tracking the activity of animals housed in confined conditions in a facility comprising:
- at least one cage;
- a plurality of antennas of the at least one cage arranged under the at least one cage;
- an RFID reader to which the plurality of antennas of the at least one cage is linked;
- a computer processor configured for controlling the RFID reader to transmit and receive;
- an RFID tag configured for being fitted to an animal housed in confined conditions in the at least one cage;
- the RFID tag comprising an antenna of the tag, separate from said plurality of antennas, and a chip both encapsulated in a capsule made from biocompatible material;
- the antenna of the tag comprising, a central plate independent from the chip, said central plate extending longitudinally and surrounded by an inner side of an open loop with two interrupted ends and comprising two elbowed stubs, said stubs extending laterally and externally from the open loop, comprising the following steps:
  - the animal is fitted with the RFID tag;
  - the RFID reader generates and emits an electromagnetic wave at the plurality of antennas of the at least one cage arranged under the at least one cage; and
  - the RFID reader identifies the one (or more than one) of the plurality of antennas of the at least one cage arranged under the at least one cage that has (have) received the response transmitted by the RFID tag such that the position of the animal is determined as a function of the antenna of the at least one cage arranged under the at least one cage or antennas of the at least one cage arranged under the at least one cage that has or have received the response transmitted by the RFID tag.

13. The method for tracking the activity of animals housed in confined conditions according to claim 12, characterized in that the surface area of the cage is less than 1 metre, the cage measuring between 10 and 30 cm wide and 25 to 75 cm long.

14. The method for tracking the activity of animals housed in confined conditions according to claim 12, wherein the plurality of antennas of the at least one cage comprises at least four antennas distributed under the cage.

15. The method for tracking the activity of animals housed in confined conditions according to claim 12, characterized in that the animal is fitted with the RFID tag by subcutaneous injection of said RFID tag, said RFID tag comprising the antenna of the tag and the chip encapsulated in a capsule made from biocompatible material.

16. The method for tracking the activity of animals housed in confined conditions according to claim 12, characterized in that the length of the open loop LLOOP is less than 20 mm, the width of the open loop WLOOP is less than 2 mm, the length of the central plate LP is less than 20 mm, the width of the central plate WP is less than 1 mm, the length of each elbowed stub Lstub is less than 1 mm.

17. The method for tracking the activity of animals housed in confined conditions according to claim 12 characterized in that the RFID tag transmits signals conveying items of information on the physiological state of the animal.

18. The method for tracking the activity of animals housed in confined conditions according to claim 12, characterized in that the computer processor configured to analyse over a given time period which of the plurality of antennas of the at least one cage arranged under the at least one cage have received a signal transmitted by the RFID tag and thus determine the successive positions of the animal.

19. The method for tracking the activity of animals housed in confined conditions according to claim 18, characterized in that the computer processor configured to determine the position of the animal by algorithms based on the triangulation methods or by positioning algorithms based on fingerprinting.

* * * * *